(12) United States Patent
Mukerjee et al.

(10) Patent No.: US 11,918,495 B2
(45) Date of Patent: Mar. 5, 2024

(54) PREVENTING STENT FAILURE USING ADAPTIVE SHEAR RESPONSIVE ENDOVASCULAR IMPLANT

(71) Applicant: LAWRENCE LIVERMORE NATIONAL SECURITY, LLC, Livermore, CA (US)

(72) Inventors: Erik V. Mukerjee, Livermore, CA (US); Jane A. Leopold, Chestnut Hill, MA (US); Amanda Randles, Durham, NC (US)

(73) Assignees: Lawrence Livermore National Security, Inc., Livermore, CA (US); The Brigham and Woman's Hoospital, Inc., Boston, MA (US); Duke University, Durham, NC (US)

( * ) Notice: Subject to any disclaimer, the term of this patent is extended or adjusted under 35 U.S.C. 154(b) by 310 days.

(21) Appl. No.: 17/374,616

(22) Filed: Jul. 13, 2021

(65) Prior Publication Data
US 2021/0338463 A1    Nov. 4, 2021

Related U.S. Application Data

(62) Division of application No. 16/251,624, filed on Jan. 18, 2019, now Pat. No. 11,083,604.

(51) Int. Cl.
*A61B 5/00* (2006.01)
*A61F 2/00* (2006.01)
(Continued)

(52) U.S. Cl.
CPC .............. *A61F 2/90* (2013.01); *A61B 5/4851* (2013.01); *A61B 5/6862* (2013.01);
(Continued)

(58) Field of Classification Search
CPC ................................ A61B 5/4851; A61B 5/68
See application file for complete search history.

(56) References Cited

U.S. PATENT DOCUMENTS

| 5,133,732 A | 7/1992 | Wiktor |
| 5,135,536 A | 8/1992 | Hillstead |

(Continued)

FOREIGN PATENT DOCUMENTS

| KR | 10-1815783 B1 | 1/2018 |
| WO | 00-10623 A1 | 3/2000 |

(Continued)

OTHER PUBLICATIONS

Assel et al. Smart Cardiovascular Stent against in Stent Restenosis. UMKC. retrieved from https://mospace.umsystem.edu/xmlui/bitstream/handle/10355/5490/SmartCardiovascularStent.pdf?sequence=5. 2010 (Year: 2010).*

(Continued)

*Primary Examiner* — Cachet I Proctor
(74) *Attorney, Agent, or Firm* — James S. Tak (57) ABSTRACT

A stent apparatus, system, and method that senses wall shear stress by measuring fluid flow at localized areas within the stent, that processes measured information through an integrated circuit, and selectively sends power to mechanically controllable stent surfaces which results in localized geometric changes. In various embodiments the stent apparatus, system, and method sends data to outside the body in real time.

10 Claims, 10 Drawing Sheets

(51) Int. Cl.
  *A61F 2/07* (2013.01)
  *A61F 2/90* (2013.01)
  *A61L 31/14* (2006.01)
  *B33Y 10/00* (2015.01)
  *A61F 2/82* (2013.01)

(52) U.S. Cl.
  CPC .............. *A61B 5/6876* (2013.01); *A61F 2/07* (2013.01); *A61L 31/14* (2013.01); *A61B 5/686* (2013.01); *A61F 2002/828* (2013.01); *A61F 2210/0014* (2013.01)

(56) References Cited

U.S. PATENT DOCUMENTS

| | | | |
|---|---|---|---|
| 5,843,120 A | 12/1998 | Israel et al. | |
| 5,935,162 A | 8/1999 | Dang | |
| 5,980,552 A | 11/1999 | Pinchasik et al. | |
| 6,790,227 B2 | 9/2004 | Burgermeister | |
| 8,308,794 B2 | 11/2012 | Martinson et al. | |
| 8,500,794 B2 | 8/2013 | Beach et al. | |
| 8,784,475 B2 | 7/2014 | Martinson et al. | |
| 9,662,021 B2 | 5/2017 | Chow et al. | |
| 11,083,604 B2 | 8/2021 | Mukerjee et al. | |
| 2005/0080346 A1* | 4/2005 | Gianchandani | B23H 9/00 623/1.15 |
| 2005/0277839 A1* | 12/2005 | Alderman | A61B 5/0031 600/481 |
| 2006/0129050 A1* | 6/2006 | Martinson | A61F 2/82 600/505 |
| 2011/0033887 A1* | 2/2011 | Fang | B81C 99/0095 73/1.01 |
| 2014/0163664 A1* | 6/2014 | Goldsmith | A61B 17/0057 604/93.01 |
| 2015/0164372 A1 | 6/2015 | Nevab et al. | |
| 2016/0038087 A1* | 2/2016 | Hunter | A61B 5/0031 623/1.1 |
| 2017/0181825 A1* | 6/2017 | Hunter | A61F 2/0059 |
| 2018/0117219 A1* | 5/2018 | Yang | C09D 167/06 |
| 2018/0192939 A1* | 7/2018 | Roth | A61B 90/06 |
| 2019/0183665 A1* | 6/2019 | Choi | A61B 18/082 |

FOREIGN PATENT DOCUMENTS

| | | |
|---|---|---|
| WO | 01-19239 A1 | 3/2001 |
| WO | 2014-144070 A1 | 9/2014 |

OTHER PUBLICATIONS

Chen et al. Enabling Angioplasty-Ready "Smart" Stents to Detect In-Stent Restenosis and Occlusion. Advanced Science. vol. 5, Issue 5. May 2018 (Year: 2018).*

International Search Report and Written Opinion for PCT/US2020/013952 corresponding to U.S. Appl. No. 16/251,624, 10 pages.

Leopold, "Pro-Healing Endothelial Progenitor Cell Capture Stents: Do the Cells Captured Explain the Clinical Outcomes?," Circ. Cardiovasc. Interv, vol. 6, No. 5, 2013, pp. 494-495.

Randles et al., "Computational Fluid Dynamics and Additive Manufacturing to Diagnose and Treat Cardiovascular Disease," Trends Bioechnol., vol. 35, No. 11, 2017, pp. 1049-1061.

Shikida et al., "Fabrication of a stent-type thermal flow sensor for measuring nasal respiration," J. of Micromech. Microeng, 20, 2020, 8 pp.

* cited by examiner

PREVENTING STENT FAILURE USING ADAPTIVE SHEAR RESPONSIVE ENDOVASCULAR IMPLANT

CROSS-REFERENCE TO RELATED APPLICATIONS

The present application is a Division of Application Ser. No. 16/251,624 filed Jan. 18, 2019 entitled "PREVENTING STENT FAILURE USING ADAPTIVE SHEAR RESPONSIVE ENDOVASCULAR IMPLANT," the disclosure of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The This invention was made with Government support under Contract No. DE-AC52-07NA27344 awarded by the United States Department of Energy. The Government has certain rights in the invention.

BACKGROUND

Field of Endeavor

The present application relates to stents and more particularly to apparatus, systems, and methods for preventing stent failure using an adaptive shear responsive endovascular implant.

State of Technology

This section provides background information related to the present disclosure which is not necessarily prior art.

When an artery lumen is partially or completely blocked and causes symptoms or ischemia, an intervention is required to open the blocked vessel and restore blood flow to the organ. This procedure is accomplished using a balloon to widen the vessel lumen that allows a stent to be implanted and function as a scaffold. Traditional metal stents are hollow, slotted, tubes with different stent strut thickness and cell shape. These stents can be coated with a polymer (biodegradable vs. permanent) and loaded with an antiproliferative-limus drug (e.g., everolimus, zotarolimus) that is eluted to prevent vascular smooth muscle cell proliferation. A second type of stent, the biodegradable vascular scaffold (BVS), uses poly-L-lactic acid as its backbone instead of metal. This stent has less rigidity than a traditional metal stent, can elute drug, and dismantles over 3-5 years leaving the artery "stent-free."

While stents are effective as vascular scaffolds to prevent abrupt closure, they are subject to failure. This may occur as a result of neointimal formation or neoatherosclerosis, which occurs in 15-30% of drug-eluting and bare metal stents, respectively. Stents are also subject to stent thrombosis, or occlusion of the stent with thrombus, which occurs at 1% in first 30 days after implantation and at a rate of 0.4-0.6%/year thereafter. In both cases of stent failure, patients may experience angina, myocardial infarction or death as the first symptom and there is a significant increase in healthcare costs associated with stent failure.

U.S. Pat. No. 9,662,021 for miniature stent-based implantable wireless monitoring devices issued May 30, 2017, provides the State of Technology information quoted and reproduced below.

"Stents have a variety of applications and are most widely used in treating obstruction of blood flow in the cardiovascular system. A common problem with stents is reocclusion, although current technologies employed to alleviate this problem include the incorporation of drug-eluting coatings as well as using careful consideration when choosing base materials. Even with these preventative measures, re-occlusion can still occur without warning since little is known about the performance of stents after initial placement."

"A device that monitors pressure in the surrounding area, as well as blood flow and temperature, would provide clinicians with a method for monitoring PADP, and therefore PCWP, and would provide information regarding how well the stent is faring in the implanted environment. Fully wireless operation as well as integration with the stent is crucial for such a device monitoring device. Current wireless cardiac pressure sensor devices require either a clinical visit or manual interrogation of the device using an external transmitter and receiver. This limits the overall effectiveness of the system by relying on the patient or a clinician to initiate collection of diagnostic data."

"What is needed therefore is a completely wireless implantable system implanted in the pulmonary artery and having fully wireless capability, in terms of both telemetry and powering, through the chest wall to record cardiac diagnostics at fixed intervals without manual intervention."

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

Applicants' apparatus, systems, and methods incorporate an adaptive design with a shear responsive sensor to mitigate the occurrence of stent failure. Applicants' apparatus, systems, and methods redesign the common stent into a novel, active, smart device, which can severely attenuate or even prevent plaque material from adhering to the lumen of the stent. This is accomplished through a distributed network of flow sensors and addressable mechanical stent surface modification regions. These are connected to a custom integrated circuit processor that can analyze the flow data and determine small changes in the stent surface to eliminate low wall shear stress areas. Eliminating low wall shear stress areas prevents plaque from adhering to solid surfaces and will inhibit restenosis from occurring.

Applicants' apparatus, systems, and methods function by sensing the wall shear stress by measuring fluid flow at localized areas at the luminal surface of the stent, processing information through an integrated circuit (comparing the data to model simulations of flow perturbation), and selectively sending power to the mechanically controllable surface which results in localized geometric changes.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Figure 1:
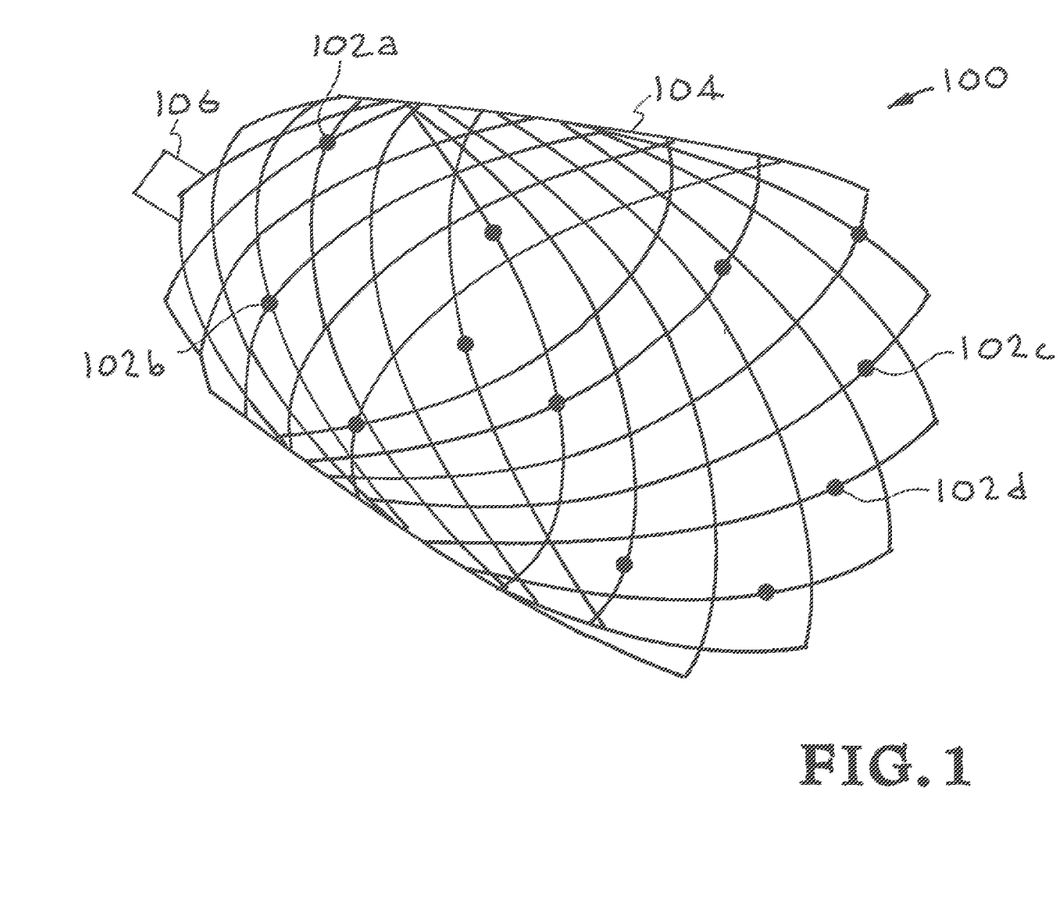
FIG. 1 illustrates one embodiment of Applicants' apparatus, systems, and methods.

Referring to FIG. 1, an illustrative view shows an embodiment of Applicants' apparatus, systems, and methods. This embodiment is identified generally by the reference numeral 100. FIG. 1 is an illustrative side view Applicants' smart stent 100. The components of Applicants' smart stent apparatus, systems, and methods 100 in FIG. 1 are listed below.
    100—Adaptive Shear Responsive Endovascular Implant (smart stent),
    102a, 102b, 102c, and 102d—Devices incorporate into the smart stent 100 during AM manufacturing,
    104—Stent lattice, and
    106—Control System (Brain).

Figure 5:
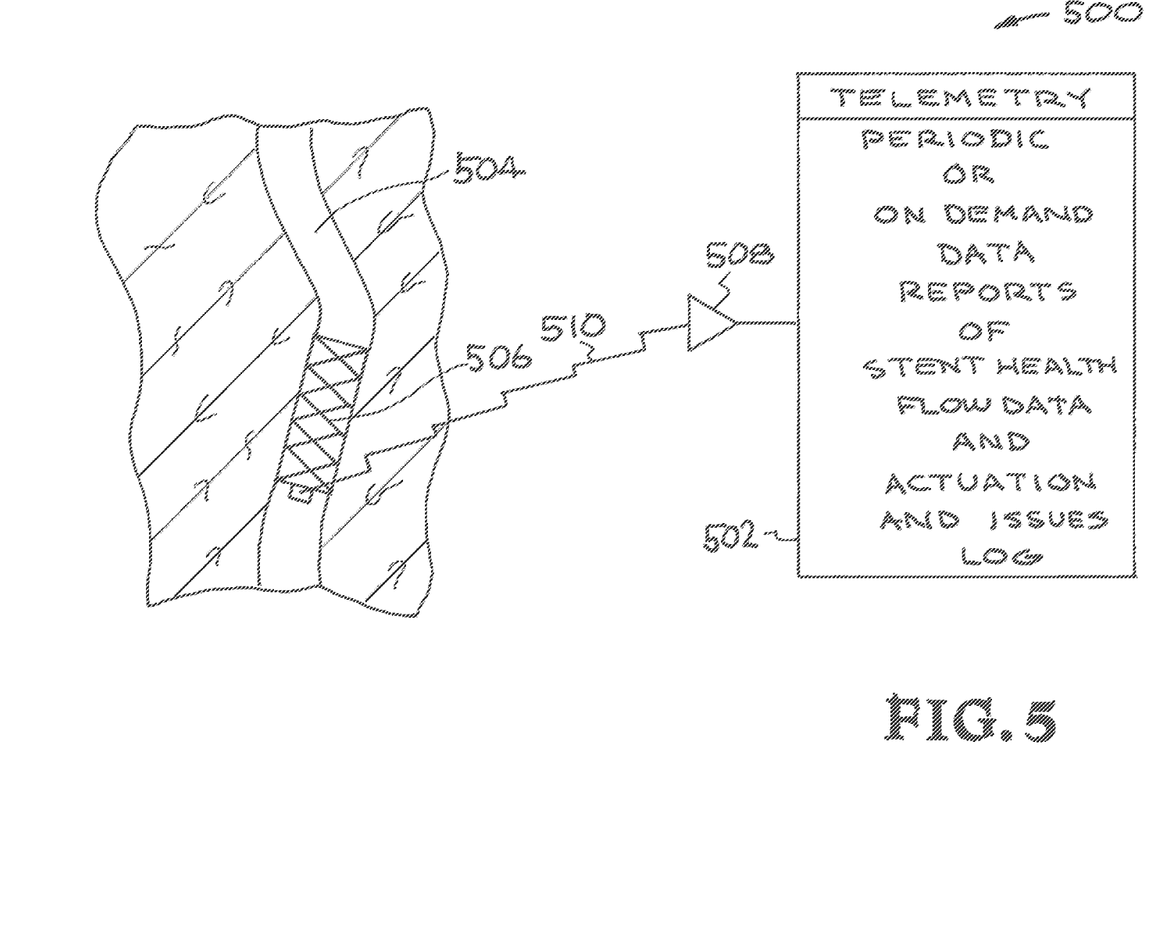
FIG. 5 is an illustrative view showing another embodiment of Applicants' apparatus, systems, and methods.

FIG. 5 is an illustrative view showing another embodiment of Applicants' apparatus, systems, and methods.

The description of the structural components of the Applicants' smart stent 100 having been completed, the operation and additional description of the Applicants smart stent will now be considered in greater detail.

The stent lattice 104 is a Shape Memory (SM) material that has basic configurations original (shape "A") and temporary (shape "B"). Changing the temperature of the stent lattice Shape Memory (SM) material 104 in conjunction with an added mechanical force changes the stent lattice 104 from original shape A to temporary shape B. Changing the temperature of the stent lattice Shape Memory (SM) material 104 also changes the stent lattice 104 from temporary shape B back to original shape A.

The devices 102a, 102b, 102c, and 102d are incorporate into the smart stent 100 during AM manufacturing. For example, the devices 102a, 102b, 102c, and 102d can be directly built in the stent lattice 104 by projection microstereolithography AM manufacturing or the micro-stereolithography AM manufacturing can produce pockets and the devices 102a, 102b, 102c, and 102d inserted in the pockets as part of the AM manufacturing process. Alternatively, the devices 102a, 102b, 102c, and 102d can be built in the stent lattice 104 by direct ink AM manufacturing. The devices 102a, 102b, 102c, and 102d can be Micro-Electro-Mechanical Systems (MEMS) that provide power and flow sensing. For example, in one embodiment the devices 102a and 102c provide flow sensing and the devices 102b and 102d are heaters that produce heat for changing the stent lattice Shape Memory (SM) material 104 from temporary shape B to original shape A.

The SMP stent structure is printed in original shape A. This shape has the super lattice structure and structural pillar areas that extend into the lumen of the stent (e.g. 102b,d). The inventors add heat to the entire 104 device along with a force to modify structural pillar areas of the lattice structure (temporary shape B—once the temperature is dropped). Under these structural pillar areas are the heaters (e.g. devices 102b,d). When individually triggered, the heat under a single structural pillar areas will cause that structural pillar area to expand locally toward the original shape A. Various embodiments will have 10's to hundreds of these structural pillar areas throughout the smart stent 100.

The Control System or Brain 106 is a printed circuit control system that receives information from the devices 102a, 102b, 102c, and 102d and analyzes the information. If a shear stress threshold is met, computational fluid simulations determine the location and magnitude of stent actuation to decrease the area of low shear stress. In one embodiment the Control System 106 is a microchip.

Applicants smart stent 100 will mitigate the occurrence of stent failure. In various embodiments Applicants' smart stent 100 can be broken down into five subunits: (1) mechanical surface, (2) processing unit, (3) power, (4) flow sensing units, and (5) telemetry. Applicants' smart stent 100 function by sensing the wall shear stress by measuring fluid flow at localized areas at the luminal surface of the stent, processing information through an integrated circuit (comparing the data to model simulations of flow perturbation), and selectively sending power to the mechanically controllable surface which results in localized geometric changes. These conformational changes will perturb the flow within the stent in result in minimizing the low wall shear stress areas. The processing unit, power and telemetry can be integrated into an ASIC chip with the necessary geometrical constraints (3 mm×3 mm×0.3 mm) for in order to use. The mechanical surface will be designed to allow for digitally addressing small pixels to allow for localized changes.

Batteries, sensors, electronic and electrode have all been implanted into humans (e.g. pace maker, deep brain stimulation, insulin pumps). The mechanical surface (the architecture of the stent structure) is a shape memory material (polymer or metal alloy), which can modify its shape on demand. Biocompatible polymers have never been used for fabricating stent structures.

SMP have basic configurations: permanent and temporary. The permanent configuration is the shape at the time of fabrication (shape "A"). Raising the temperature of the SMP above the glass transition temperature ("critical temperature", Tc), applying a mechanical load, and lowering the temperature locks the SMP into a temporary configuration (shape "B"). Reconfiguring the material from shape "B" to shape "A" requires that the material be heated near or above the critical temperature. Typically, the material is a whole structure process (ie. The entire structure is heated and the whole structure transitions back to shape "A"). If one would think of a sheet of shape memory polymer (SMP) "paper" with text, Applicants' system could locally change the shape under the dot of an "i" or an "o" (and not the entire structure). Thus, by providing local changes there is sufficient resolution for manipulating blood flow within the stent.

Geometrical and power requirement set strict upper bounds on the limitations of Applicants' flow sensor. A MEMS based hot film/wire anemometer (1 mm×1 mm×0.2 mm) will address both of these requirements. An anemometer comprises 2 heater elements (1 to inject energy into the system and 1 to measure that energy downstream). By precisely controlling the amount of energy added to the system and the distance between the elements, one can calculate the velocity by measuring the delta time between injection and sensing of that energy. Controlling the sensor distance from the arterial wall (r), one can calculate the wall shear (dV/dr).

In various embodiments, Applicants' smart stent identifies and attenuates regions of low shear stress in the lumen of a stent through an integrated, distributed network of flow sensors; a custom signal processing unit; and a power supply that selectively sends power to a mechanically controllable stent matrix which results in localized geometric changes. The distributed network of flow sensors maps the hemodynamic flow with the stent. This data is sent to the processing unit and analyzed. If a shear stress threshold is met, computational fluid simulations determine the location and magnitude of stent actuation to decrease the area of low shear stress. The stent device operates as an autonomous closed loop system. The incorporation of telemetry allows for periodic or on demand data reports of stent health, flow data, and actuation and issues logs.

Atherosclerotic coronary heart disease is the leading cause of morbidity and mortality in the United States and is responsible for >1 million myocardial infarctions and coronary heart disease-related deaths annually. Current clinical practice is based on treating established atherosclerotic disease since there is a knowledge gap in methodology to predict where coronary atherosclerotic plaques will develop and no mechanism to intervene and alter the natural biology of the disease. To address this, Applicants have taken a revolutionary approach to prevent atherosclerosis in coronary arteries by implanting a shape-morphing stent with a shear stress sensor in atheroprone areas of the coronary tree. This endovascular implant reports coronary shear stress and actuate (change shape) in response. The endovascular implant report is in real time.

Applicants' apparatus, systems, and methods are designed to function as a dynamically modifiable endovascular stent or scaffold that can be implanted into any vascular bed >1 mm in diameter, other extra-vascular sites where stents have been used for off-label indications, and can be scaled to the largest vessels in the body. Applicants' apparatus, systems, and methods can also be adapted to serve as the scaffold for a heart valve such as that used in surgical or percutaneous valve replacement in the aortic, mitral, tricuspid, or pulmonary positions. Applicants' apparatus, systems, and methods is made of a non-thrombotic biocompatible material that can be adapted to elute antiproliferative drugs and has a sensor that measures hemodynamic parameters (e.g., flow, wall shear stress), reports these parameters to an external monitor, and then based on this data, can actuate a shape change in the stent/scaffold. The sensor can be adapted to monitor other physical, cellular, biological, or molecular factors in the bloodstream such as glucose, potassium, or temperature.

As a therapeutic device, Applicants' apparatus, systems, and methods is used in conjunction with current percutaneous interventional techniques to treat symptomatic atherosclerotic vascular disease in the coronary arteries, cerebral vasculature, and peripheral vasculature. Applicants' apparatus, systems, and methods invention can also be used to treat vascular aneurysms, coarctation, or other vascular narrowings. Applicants' apparatus, systems, and methods can also be used in the pulmonary vasculature in pulmonary arterial hypertension, combined post- and pre-capillary pulmonary hypertension, chronic thromboembolic pulmonary hypertension as well as in the systemic and pulmonary venous and lymphatic systems. Applicants' apparatus, systems, and methods can also be used in any other area where a stent has been used, such as the heart or extra-vascular spaces, such as the airways.

Applicants' apparatus, systems, and methods can also be used as a preventative device by endovascular implantation in the arterial, venous, or lymphatic system to prevent the development of vascular diseases that narrow or increase the vessel lumen and wall such as atherosclerosis, aneurysm formation, or vessel/lymphatic narrowing.

Figure 2A:
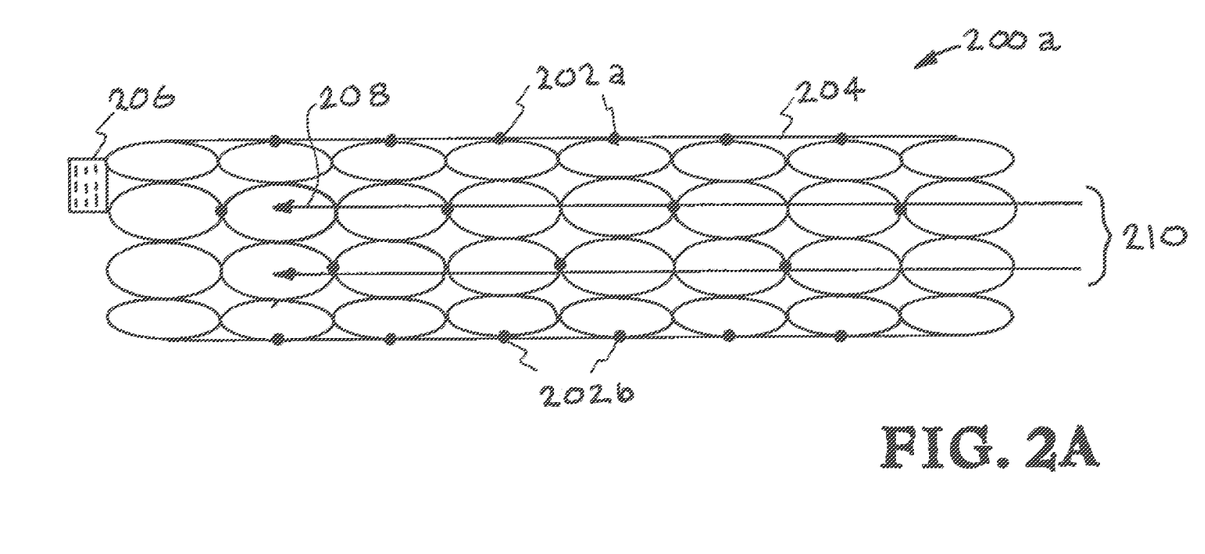
FIGS. 2A, 2B, and 2C are illustrative views of Applicants' apparatus, systems, and methods.
Figure 2B:
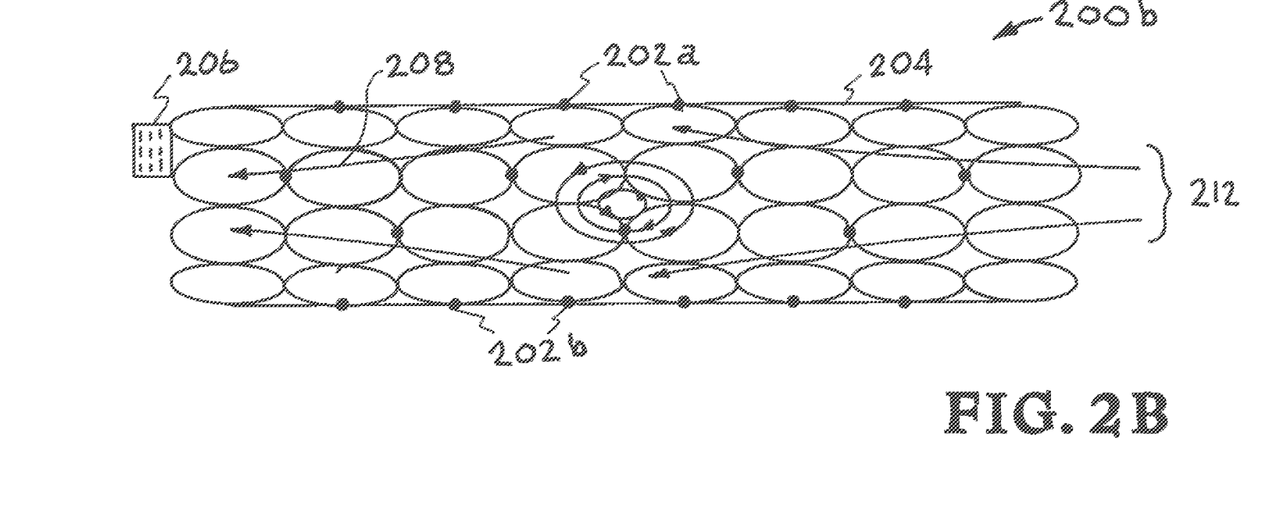
Figure 2C:
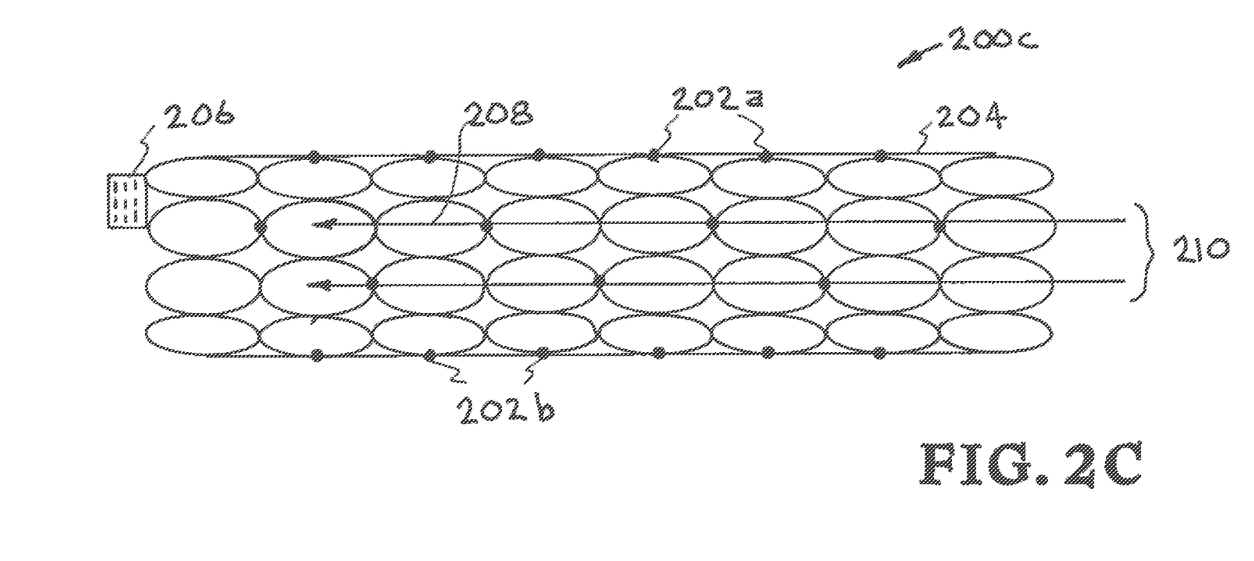

Referring to FIGS. 2A, 2B and 2C; illustrative side views show Applicants' smart stent 100 as it would operate in a coronary artery. The components of Applicants' smart stent 100 shown in FIGS. 2A, 2B and 2C are listed below.

200a—Initial view of smart stent in an artery,
    200b—View of smart stent detecting turbulent flow in artery,
    200c—View of smart stent with corrected stent shape,
    202a—Flow sensors,
    202b—Heaters,
    204—Stent body,
    206—Control system (Brain),
    208—Flow direction,
    210—Normal flow, and
    212—Turbulent flow area.

The identification and description of the structural components of the Applicants' smart stent having been completed, the operation and additional description of the Applicants smart stent will now be considered in greater detail.

FIG. 2A is an illustrative side view of Applicants' smart stent as it would function in an artery. This view is designated generally by the reference numeral 200a. The arrows 208 indicate flow direction. FIG. 2A shows normal flow 210 that is sensed by flow sensors 202a. The heaters 202b and the control system (brain) 206 are part of the smart stent.

FIG. 2B is an illustrative side view of Applicants' smart stent wherein the smart stent has detected turbulent flow 212. This view is designated generally by the reverence numeral 200b. The turbulent flow 212 can be created by the start of plaque buildup in the stent, by undesirable shape changes in the stent body 204, or by other conditions. In this view 200b the smart stent flow sensors 202a signal to the control system 206 allows the control system 206 to detect the turbulent flow 212. If the conditions that created the turbulent flow 212 continued it could lead to failure of the stent; however, with Applicants' smart stent apparatus, systems, and methods the turbulent flow is detected and stent body 204 adjusted to eliminate the turbulent flow 212. The control system (brain) 206 of Applicants' smart stent retrieves data from the flow sensors 202a, compares the data to model simulations of flow perturbation, and selectively sends signals to the heaters 202b to activate the heaters 202b. Heat produced by the heaters 202b adjusts the mechanically controllable sections of the stent body 204 resulting in localized geometric changes that eliminates the turbulent flow 212.

The stent body 204 lattice is made of a Shape Memory (SM) material that has basic configurations original (shape "A") and temporary (shape "B"). Changing the temperature of the stent lattice Shape Memory (SM) material provides an added mechanical force changing the stent lattice from original shape A to temporary shape B. Changing the temperature of the stent lattice Shape Memory (SM) material also changes the stent lattice from temporary shape B back to original shape A.

FIG. 2C is an illustrative side view of Applicants' smart stent after it has been adjusted to eliminate the turbulent flow 212. This view is designated generally by the reference numeral 200c. FIG. 2C shows normal flow 210 has returned.

Figure 3A:
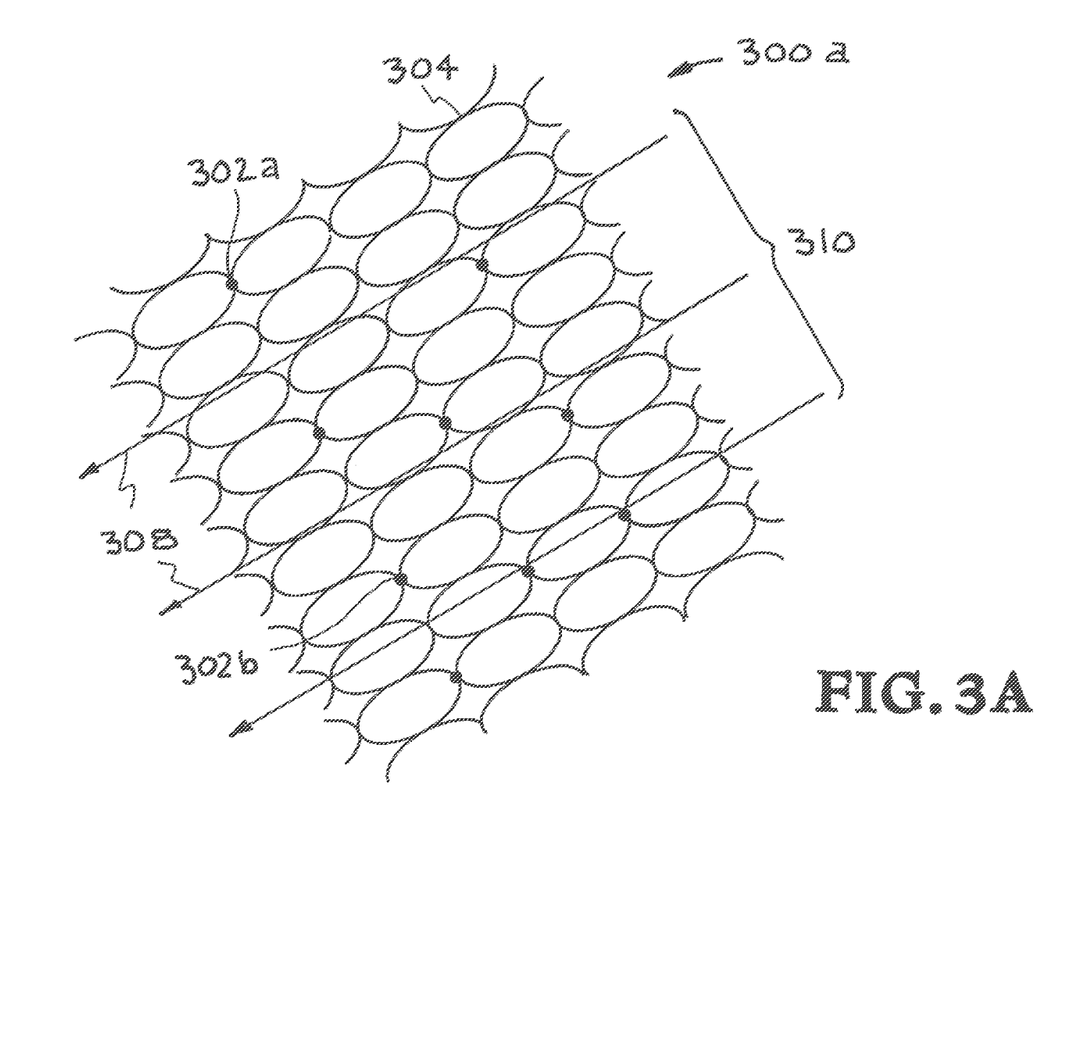
FIGS. 3A, 3B, and 3C are illustrative sectional views of Applicants' apparatus, systems, and methods.
Figure 3B:
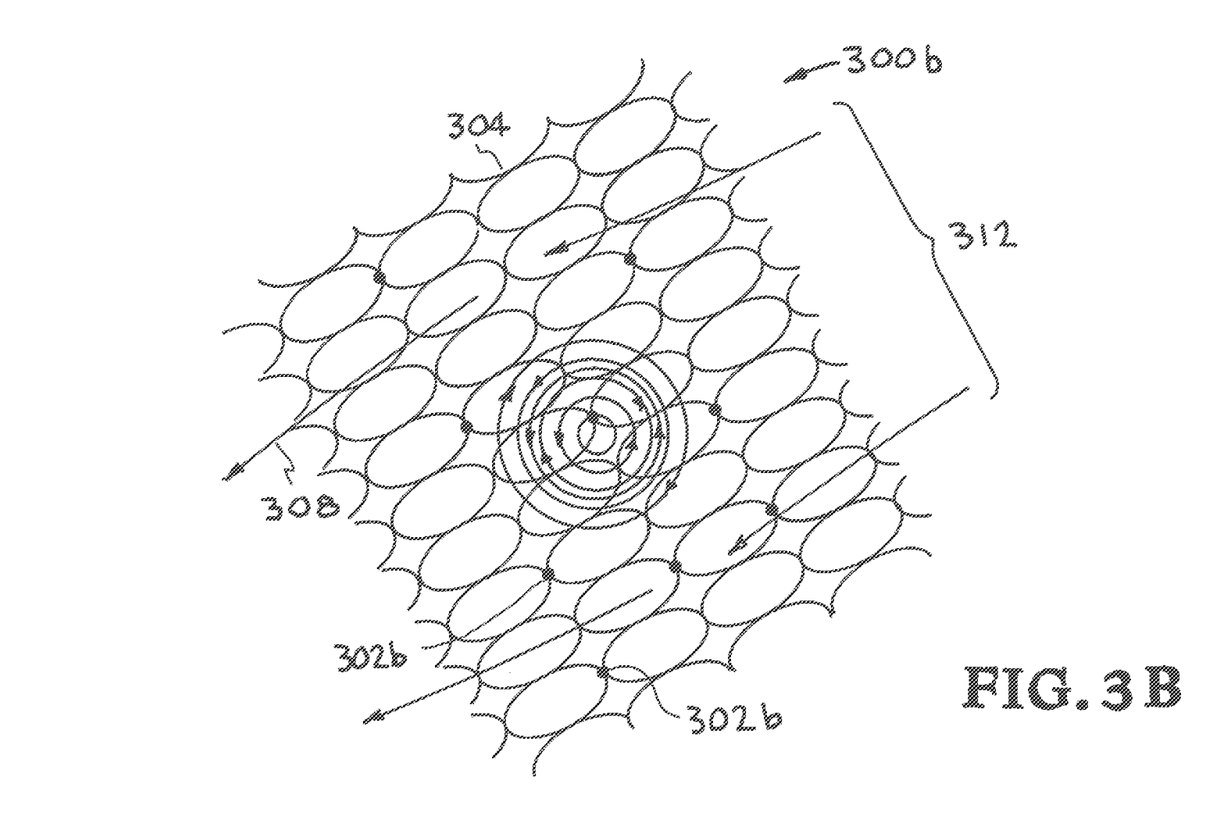
Figure 3C:
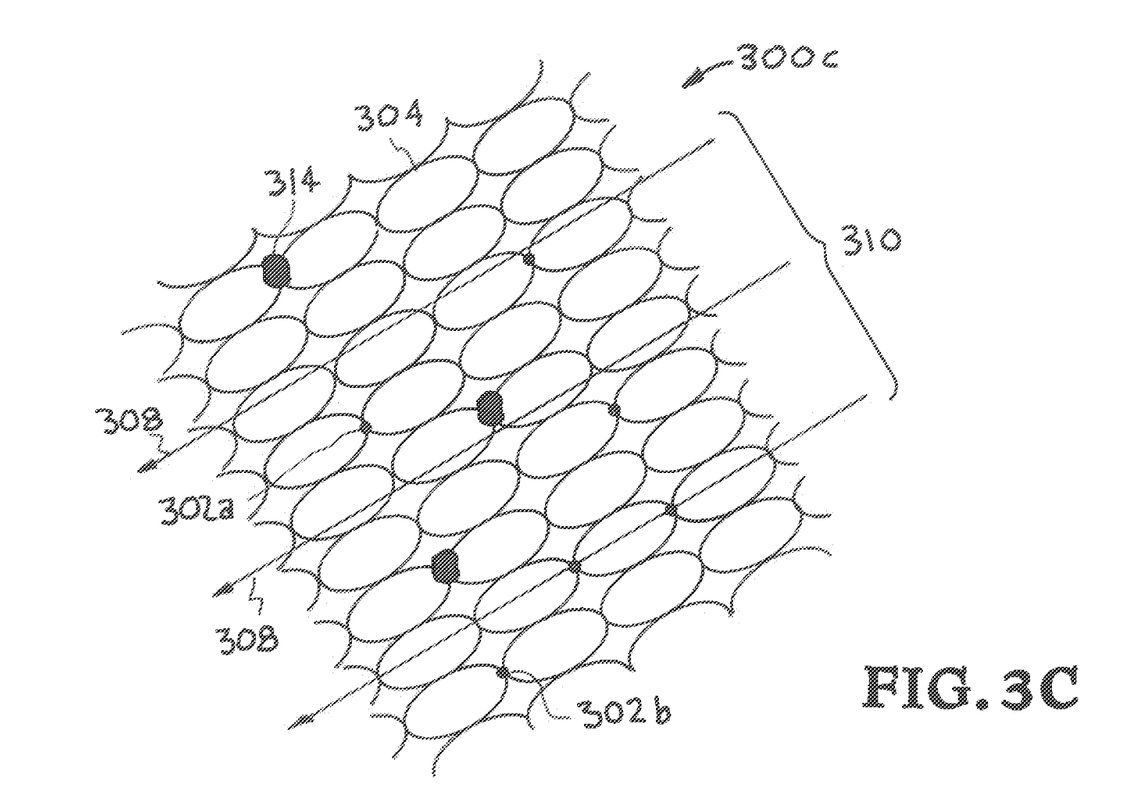

Referring to FIGS. 3A, 3B and 3C; additional illustrative views show a section (in the middle) of Applicants' smart stent illustrated in FIGS. 2A, 2B and 2C with the sections laid flat. The components of Applicants' smart stent shown in FIGS. 3A, 3B and 3C are listed below.

300a—Initial view of smart stent showing normal flow,
300b—View of smart stent detecting turbulent flow,
300c—View of smart stent with corrected stent shape,
302a—Flow sensors,
302b—Heaters,
304—Stent body,
308—Flow direction,
310—Normal flow,
312—Turbulent flow area, and
314—Pillars (the pillars represent changes in the physical structure).

The identification and description of the structural components of the Applicants' smart stent having been completed, the operation and additional description of the Applicants smart stent will now be considered in greater detail.

FIG. 3A shows a section (from the middle) of Applicants' smart stent illustrated in FIG. 2A with the section laid flat. This view is designated generally by the reference numeral 300a. The arrows 308 indicate flow direction. FIG. 3A shows normal flow 310 that is sensed by flow sensors 302a. The heaters 302b and the control system (brain) 306 are part of the smart stent.

FIG. 3B shows a section (from the middle) of Applicants' smart stent illustrated in FIG. 2B with the section laid flat. This view is designated generally by the reverence numeral 300b. The turbulent flow 312 can be created by the start of plaque buildup in the stent, by undesirable shape changes in the stent body 304, or by other conditions. In this view 300b the smart stent flow sensors 302a signal to the control system 306 allows the control system 306 to detect the turbulent flow 312. If the conditions that created the turbulent flow 312 continued it could lead to failure of the stent; however, with Applicants' smart stent apparatus, systems, and methods the turbulent flow is detected and stent body 304 adjusted to eliminate the turbulent flow 312. The control system (brain) 306 of Applicants' smart stent retrieves data from the flow sensors 302a, compares the data to model simulations of flow perturbation, and selectively sends signals to the heaters 302b to activate the heaters 302b. Heat produced by the heaters 302b adjusts the mechanically controllable sections of the stent body 304 resulting in localized geometric changes that eliminates the turbulent flow 312.

FIG. 3C shows a section (from the middle) of Applicants' smart stent illustrated in FIG. 2C with the section laid flat. This view is designated generally by the reference numeral 300c. The Pillars 314 are stylized illustrations that represent changes in the physical structure of the stent body 304 web. FIG. 3C shows that normal flow 310 has returned.

Figure 4A:
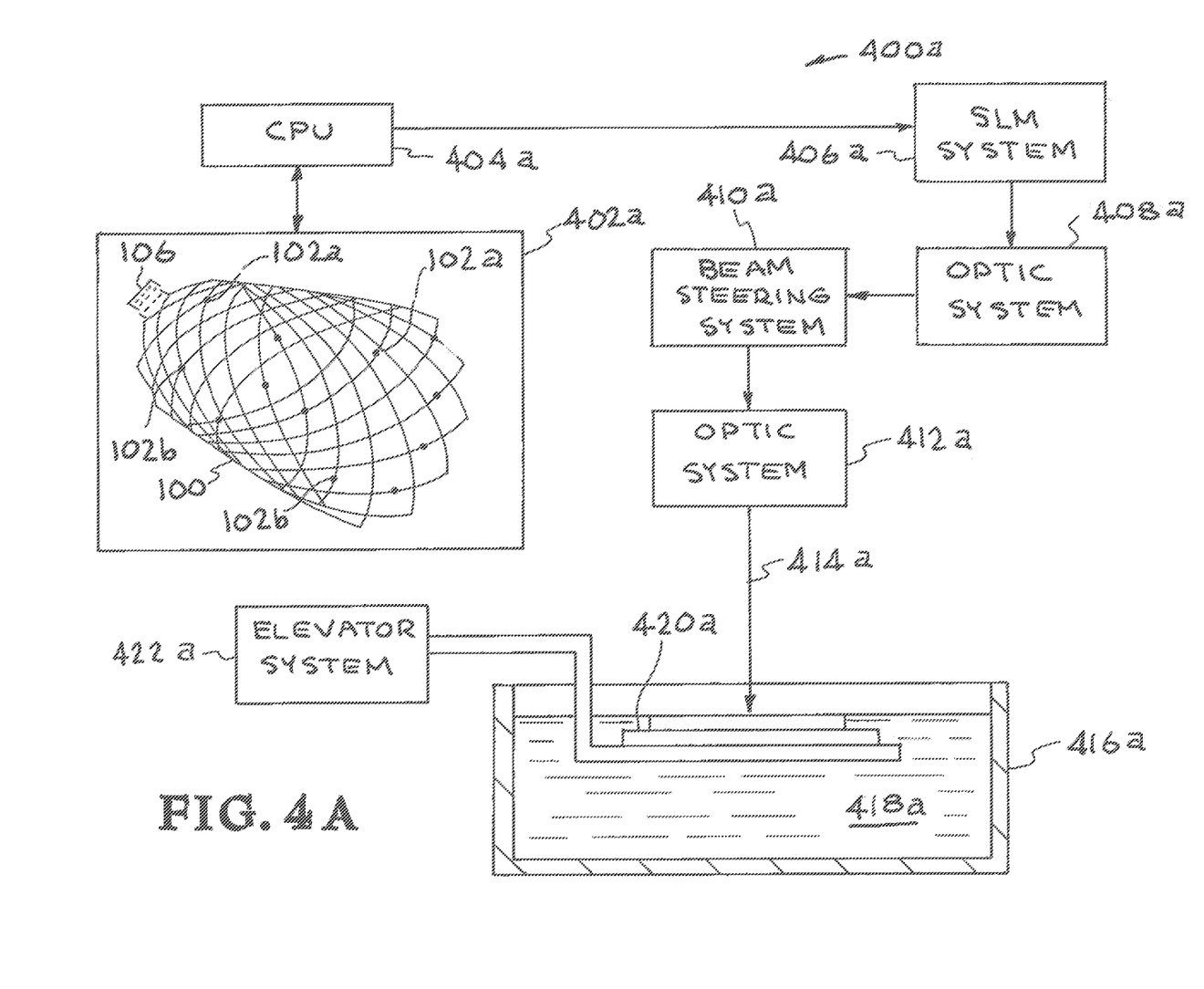
FIGS. 4A and 4B illustrate embodiments of additive manufacturing systems for making the smart stent.

Referring now to FIG. 4A, a first embodiment of an additive manufacturing system for making the smart stent of FIG. 1 is illustrated. This embodiment of the additive manufacturing system is designated generally by the reference numeral 400a. This embodiment of the additive manufacturing system 400a is a projection micro-stereolithography system. One version of the additive manufacturing system 400a is a Large Area Projection Micro-Stereolithography (LAPuSL) system. The additive manufacturing system 400a produces the smart stent 100. The structural elements of the additive manufacturing system 400a are identified and described below.

Reference numeral 400a—Additive manufacturing system.
Reference numeral 402a—3-D computer generated model of stent 100.
Reference numeral 404a—CPU.
Reference numeral 406a—SLM system.
Reference numeral 408a—Optics system.
Reference numeral 410a—Beam directing optics.
Reference numeral 412a—Optics system.
Reference numeral 414a—Projected image.
Reference numeral 416a—Reservoir.
Reference numeral 418a—Bath.
Reference numeral 420a—Substrate.
Reference numeral 422a—Elevator system.

The structural elements of the system 400a having been identified and described, the operation of the system 400a will now be considered. Initially, a three-dimensional model 402a of the smart stent 100 is produced in a computer readable format. The model 402a will be used by the additive manufacturing system 400a to produce the stent 100. The three-dimensional model 402a of the stent 100 can be produced by 3-D CAD system.

The three-dimensional model 402a is sent to the CPU 404a. The three-dimensional model is digitally sliced into layers by the CPU 404a. The layers are sent to the SLM system 406a and subsequently thru 408a, 410a, and 412a to be projected 414a to their appropriate locations on the moveable substrate 420a.

The layers are sent from the CPU 404a to the SLM system 406a. The layers are sent from the SLM system 406a to the Optics system 408a. The layers are sent from the Optics system 408a to the Beam directing optics 410a. The layers are sent from the Beam directing optics 410a to the Optics system 412a. The Optics system 412a produces a Projected image 414a into the Bath 418a in the Reservoir 416a. The first layer is produced on the substrate 420a.

The Projected image 414a is an image beam that is directed onto the build plane to cure the curable monomer material of the Bath 418a in the Reservoir 416a and produce individual layers of the stent 100. The elevator system 422a sequentially lowers the layers into the curable monomer bath 418a to allow a fresh layer of curable monomer material to coat the previous layer. The steps for all slices are repeated to complete the stent 100.

Figure 4B:
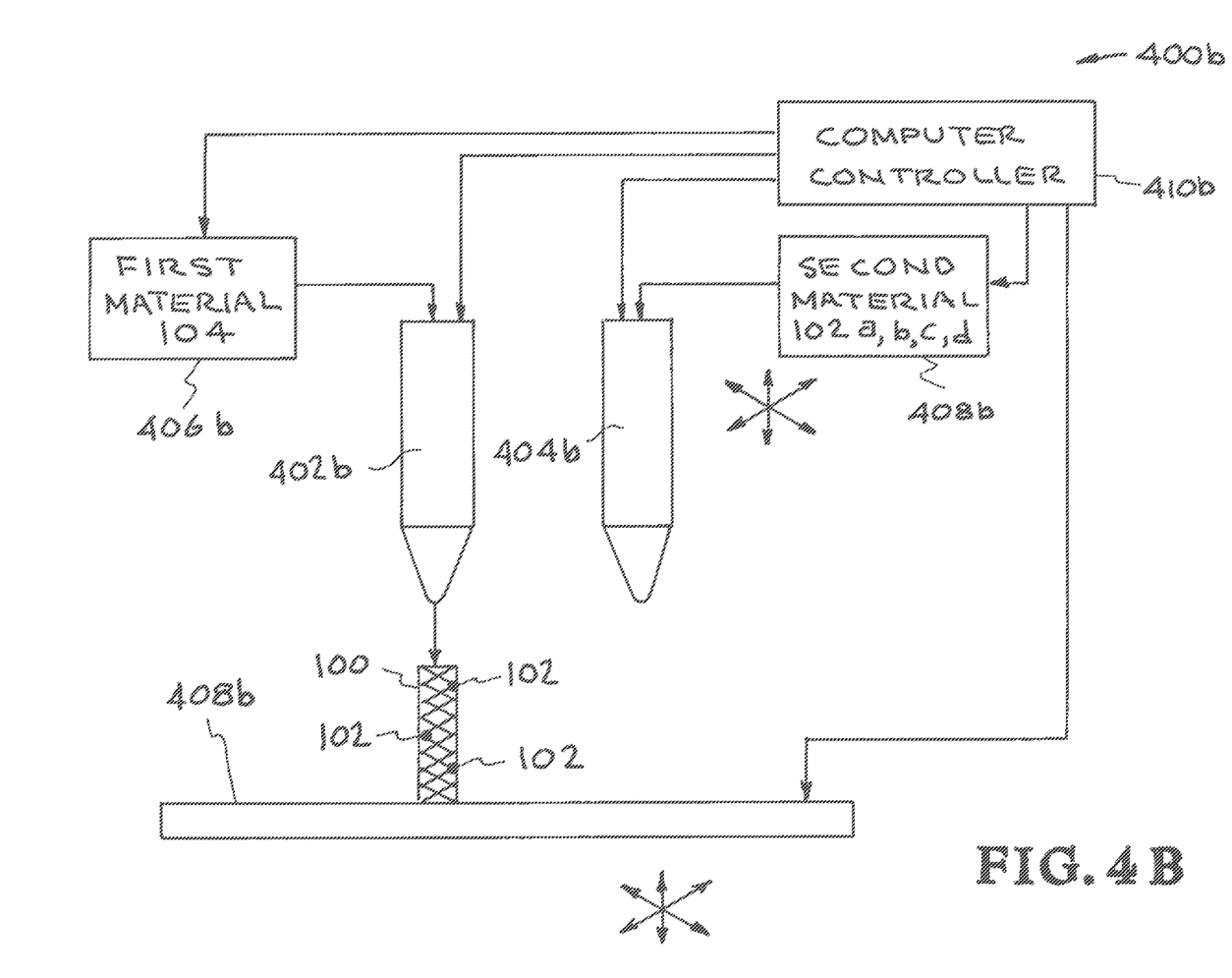

Referring now to FIG. 4B, another embodiment of an additive manufacturing system for making the smart stent 100 of FIG. 1 is illustrated. This embodiment of the additive manufacturing system is designated generally by the reference numeral 400b. The additive manufacturing system 400b produces the smart stent 100.

The additive manufacturing system 400b uses state of the art 3-D printing technology to produce the smart stent 100. Initially, a three-dimensional model of the smart stent 100 is produced in a computer readable format. The model is used by the additive manufacturing system 400b to control the components of the 3-D printing system. The additive manufacturing system 400b uses two head disposition printing to build the smart stent 100 on a substrate 408b. The system 400a uses one head 402a for producing the web 104 and the other head 404b for depositing the MEMS 102(a,b,c,d) in the web 104. The computer controller 410b provides instructions for the 3D printing.

As illustrated in FIG. 4B, one of the print heads 402b obtains web material from a web material supply source 406b. The print head 402b uses the web material to print the web 104. The other of the print head 404b obtains MEMS devices 102(a,b,c,d) from a supply source 408b. The print head 404b deposits the MEMS devices 102(a,b,c,d) in the web 104. The smart stent 100 is printed one layer at a time wherein each layer includes the predetermined portions of the web 104 and the MEMS devices 102(a,b,c,d) as dictated by the three-dimensional model of the smart stent 100. The layers are built on the substrate 408b.

Referring to FIG. 5; an illustrative view show another embodiment of Applicants' apparatus, systems, and methods. This embodiment is identified generally by the reference numeral 500. The components of Applicants' smart stent apparatus, systems, and methods 500 shown in FIG. 5 are listed below.
- 502—telemetry,
- 504—vascular bed, and
- 506—smart stent,
- 508—receiver, and
- 510—signal.

The description of the structural components of the Applicants' smart stent apparatus, systems, and methods 500 having been completed, the operation and additional description of the Applicants smart stent will now be considered in greater detail. The smart stent 506 is shown implanted in a vascular bed 504. The smart stent 506 functions by measuring fluid flow at localized areas within the stent, processing information through an integrated circuit (comparing the data to model simulations of flow perturbation), and selectively sending power to the mechanically controllable surface which results in localized geometric changes. The smart stent 506 transmits data to the telemetry module 502 that controls the operation of the smart stent 506 and analyzes the data. The telemetry module 502 compares the data to model simulations and selectively sends power to MEMS units that mechanically control the stent web and provide localized geometric changes in the stent web to correct for changes in flow due to plaque buildup. The telemetry module 502 can provide "periodic" or "on demand" reports.

The smart stent 506 identifies and attenuates regions of low shear stress in the lumen of a stented blood vessel through an integrated, distributed network of flow sensors, a custom signal processing unit, power supply and telemetry into the shape memory polymer stent. The distributed network of flow sensors maps the hemodynamic flow with the stent. This data is sent to the processing unit and analyzed. If a shear stress threshold is met, computational fluid simulations determine the location and magnitude of stent actuation to decrease the area of low shear stress. The stent device operates as an autonomous closed loop system. The incorporation of telemetry allows for periodic or on demand data reports of stent health, flow data, and actuation and issues logs.

As a therapeutic device, Applicants' apparatus, systems, and methods is used in conjunction with current percutaneous interventional techniques to treat symptomatic atherosclerotic vascular disease in the coronary arteries, cerebral vasculature, and peripheral vasculature. Applicants' apparatus, systems, and methods invention can also be used to treat vascular aneurysms, coarctation, or other narrowings or dilations. Applicants' apparatus, systems, and methods can also be used in the pulmonary vasculature in pulmonary arterial hypertension, combined post- and pre-capillary pulmonary hypertension, chronic thromboembolic pulmonary hypertension as well as in the pulmonary and systemic venous and lymphatic systems. Applicants' apparatus, systems, and methods can also be used in any other area where a stent has been used, such as the heart or extra-vascular spaces, such as the airways. Applicants' apparatus, systems, and methods can also be used as a preventative device by endovascular implantation in the arterial, venous, or olymphatic system to prevent the development of atherosclerosis, aneurysm formation, or vessel/lymphatic narrowing.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A method of making a stent, comprising the steps of:
using additive manufacturing to produce a stent lattice made of shape memory material,
using additive manufacturing to produce a multiplicity of heaters connected to said stent lattice,
using additive manufacturing to provide a multiplicity of flow sensors that are operatively connected to said stent lattice,
and
using additive manufacturing to provide a control system that is operatively connected to said stent lattice, that is operatively connected to said multiplicity heaters, and that is operatively connected to said multiplicity of flow sensors.

2. The method of making a stent of claim 1 wherein said step of providing a multiplicity of flow sensors that are operatively connected to said stent lattice comprises the steps of using additive manufacturing to provide a multiplicity of individual pockets for individual flow sensors and inserting an individual flow sensor in said individual pocket.

3. The method of making a stent of claim 1 wherein said step of using additive manufacturing to provide a control system that is operatively connected to said stent lattice comprises the steps of using additive manufacturing to provide a pocket for a control system and inserting said control system in said pocket.

4. The method of making a stent of claim 1 wherein said control system is a microchip and wherein said step of inserting said control system in said pocket comprises inserting said microchip in said pocket.

5. The method of making a stent of claim 1 wherein said control system is a microchip and wherein said step of using additive manufacturing to produce a control system connected to said stent lattice comprises using additive manufacturing to produce a microchip connected to said stent lattice.

6. The method of making a stent of claim 1 further comprising the steps of
providing a telemetry unit connected to said stent body and operatively connected to said multiplicity of flow sensors, said multiplicity of heaters, and said control system; and
providing a remotely located receiving unit wherein said flow sensors and said control system collects information, wherein said telemetry unit transmits said information, and wherein said remotely located receiving unit receives said information.

7. The method of making a stent of claim 6 wherein said remotely located receiving unit and said telemetry unit provides periodic reports with said information.

8. The method of making a stent of claim 6 wherein said remotely located receiving unit and said telemetry unit on demand periodic reports with said information.

9. The method of making a stent of claim 6 wherein said information is information on stent health and wherein said remotely located receiving unit and said telemetry unit provides periodic reports or on demand reports with said information on stent health.

10. The method of making a stent of claim 6 wherein said information is flow data information and wherein said remotely located receiving unit and said telemetry unit provides periodic reports or on demand reports with said flow data information.

\* \* \* \* \*